United States Patent
Steffenino et al.

(10) Patent No.: US 6,902,609 B2
(45) Date of Patent: Jun. 7, 2005

(54) PEARLESCENT FILM COATING SYSTEMS AND SUBSTRATES COATED THEREWITH

(75) Inventors: Rita M. Steffenino, Green Lane, PA (US); Franklin J. Gulian, Schwenksville, PA (US); Irvin M. Lash, Pennsburg, PA (US); Thomas P. Farrell, Warrington, PA (US); Charles D. Fields, West Mailing (GB)

(73) Assignee: BPSI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/778,600

(22) Filed: Feb. 13, 2004

(65) Prior Publication Data

US 2004/0182283 A1 Sep. 23, 2004

Related U.S. Application Data

(60) Provisional application No. 60/448,990, filed on Feb. 20, 2003.

(51) Int. Cl.$^7$ .................. C09D 5/36; C09D 101/00; C09D 101/26; C09D 101/28; C09D 105/00
(52) U.S. Cl. ............... 106/162.8; 106/162.9; 424/476; 424/480; 427/2.23; 427/415; 426/103; 426/302; 426/303; 426/304
(58) Field of Search ................ 426/103, 302, 426/303, 304; 427/2.23, 415; 424/476, 480; 106/162.8, 175.1, 181.1, 203.1, 204.3, 217.7, 217.9, 204.01

(56) References Cited

U.S. PATENT DOCUMENTS

| | | |
|---|---|---|
| 3,087,827 A | 4/1963 | Klenke, Jr. et al. |
| 3,087,828 A | 4/1963 | Linton |
| 3,087,829 A | 4/1963 | Linton |
| 4,576,646 A | 3/1986 | Branco et al. |
| 4,725,441 A | 2/1988 | Porter et al. |
| 4,931,286 A | 6/1990 | Johnson et al. |
| 5,470,581 A | 11/1995 | Grillo et al. |
| 5,611,851 A | 3/1997 | DeLuca et al. |
| 5,858,078 A * | 1/1999 | Andes et al. ............... 106/437 |
| 6,348,090 B1 | 2/2002 | Grillo et al. |
| 6,420,473 B1 | 7/2002 | Chittamuru et al. |
| 6,627,212 B2 | 9/2003 | Uzunian et al. |

FOREIGN PATENT DOCUMENTS

WO    WO 00/03609    1/2000

OTHER PUBLICATIONS

"Candurin® Unique Pigments"–Marketing Brochure Published by Merck KgaA (ca. 2000), no month provided.

* cited by examiner

*Primary Examiner*—David Brunsman
(74) *Attorney, Agent, or Firm*—Muserlian, Lucas and Mercanti, LLP

(57) ABSTRACT

The present invention is directed to film coating systems for use on oral dosage forms such as compressed tablets and orally-ingestible substrates which have improved pearlescent qualities. The film coating systems can be applied either directly to a substrate or after the substrate has been coated with a subcoat. In preferred aspects, the pearlescent film coating is prepared as a dry powder mixture containing a cellulosic polymer, a detackifier, a gloss enhancer, and a pearlescent pigment. Film coating compositions containing an aqueous suspension of the powder mixtures, methods of applying the coatings to substrates and the coated substrates are also disclosed.

48 Claims, No Drawings

PEARLESCENT FILM COATING SYSTEMS AND SUBSTRATES COATED THEREWITH

CROSS-REFERENCE TO RELATED APPLICATIONS

This application claims the benefit of priority from U.S. Provisional Application Ser. No. 60/448,990, filed Feb. 20, 2003, the contents of which are incorporated herein by reference.

BACKGROUND OF THE INVENTION

1. Field of the Invention

The present invention relates to film coatings having improved pearlescent qualities. The invention also relates to pharmaceutical substrates having such film coatings and methods of preparing the same.

2. Description of the Prior Art

Over the years, considerable effort has been expended to increase the visual appeal of tablets and capsules. Many pharmaceutical manufacturers attempt to establish brand identity for their newly-approved products by altering the shapes, colors, etc. of the dosage forms. It has been proposed that consumers develop greater brand loyalty for distinctively appearing products as compared to those containing the same active ingredient in an unremarkable appearance, i.e. a white compressed tablet.

It has also been proposed that imparting a pearlescent appearance to tablets, etc would provide a means of further differentiating new products, even from those having a bright or highly polished finish coat. One such coating currently marketed to provide a pearlescent or nacreous quality to various products is sold under the trade name Candurin® by Merck KGaA. The pearlescent pigments are titanium oxide and/or iron oxide pigments supported on a base of lamellar substrate comprising mica or flakes of $Al_2O_3$, $SiO_2$ or $TiO_2$.

PCT patent application having publication number WO 00/03609 discloses coated articles prepared using Candurin pearlescent pigments. Among the articles coated are sugar products (e.g. caramel), cake decorations, chewing gum, chocolate, ice cream, cereals, snack products, nonpareils, gelatin products, candy, licorice, icing, cream compositions, tablets and capsules. The coating materials which can be included with the pearlescent pigments are sugars, shellacs (both aqueous and ethanolic), polymethacrylates and "cellulose types" including specifically hydroxypropylmethylcellulose (HPMC) and Sepifilm® LP (HPMC, microcrystalline cellulose (MCC) and stearic acid). Although the publication discloses addition of conventional colorants to the pearlescent compositions, there is no mention of how to obtain a high gloss finish on pharmaceutical dosage forms, either by formula or process modifications/optimizations.

Additionally, U.S. Pat. No. 6,627,212 discloses of using special effects pigments in ingestible drugs. Examples include mixtures of platy titanium dioxide pigments, titanium dioxide and/or iron oxide coated on inorganic platy substrates and combinations thereof, with ingredients, such as carnauba wax, isopropyl alcohol, and gelatins, to impart an optical effect to the coated and/or imbedded articles. Once again, however, there is no mention of how to obtain a high gloss finish on pharmaceutical dosage forms.

Other attempts have been made at improving the appearance of tablets. For example, U.S. Pat. No. 4,576,646 discloses providing tablets with a coating having a satin appearance. In addition, commonly assigned U.S. Pat. No. 6,420,473 discloses acrylic enteric coating compositions which can contain, inter alia a pearlescent pigment based on mica and/or titanium dioxide. Coatings produced from these formulations, however, have relatively low gloss. Enteric coating compositions are highly specialized to assist in delivering a pharmaceutical active to the intestines and, therefore, not generally applicable to immediate release dosage forms. Due to the physical characteristics of typical enteric coating systems, the coating finish is generally of low gloss.

In spite of the foregoing, further improvements have been sought. For example, it has been found that it would be desirable to provide a higher gloss finish for tablets and other substrates having pearlescent coatings. The present invention addresses this and other needs.

SUMMARY OF THE INVENTION

In one aspect of the invention there are provided dry powder mixtures useful in preparing film coating compositions for the pharmaceutical, confection and related arts. The powder mixture or blend includes a cellulosic polymer, a detackifier, a gloss enhancer or enhancers and a pearlescent pigment. In preferred aspects of this embodiment, the cellulosic polymer is sodium carboxymethylcellulose (Na CMC), the detackifier is lecithin, and the gloss enhancers are maltodextrin, or dextrose or combinations of the two. Suitable maltodextrins and dextrose include those commercially available and approved for use in the food and pharmaceutical arts. Preferred pearlescent pigments include titanium dioxide platelets (also known as platy $TiO_2$) or micaceous based pearlescent pigments.

In another aspect of the invention, there are provided pearlescent film coating compositions containing suspensions of one or more powder mixtures described above. The suspensions preferably contain from about 2 to about 20% solids content. Still further aspects include methods of coating orally-ingestible edible substrates with the pearlescent pigment-containing suspension and an optional subcoating, as well as the coated substrates prepared by these methods.

As a result of the present invention, several advantages and improvements over the prior art are realized. For example, the artisan is now able to provide film coated ingestible products having higher degrees of pearlescence and shine. In addition, the pearlescent systems of the present invention possess excellent oxygen barrier properties. Thus, it is possible to provide not only pleasing aesthetic appearance, but also functional protection for oxygen-labile cores.

For purposes of the present invention "orally-ingestible substrate" shall be understood to mean any pharmaceutically acceptable dosage form, e.g. tablet, capsule, caplet, etc. or any other veterinary or confectionary product capable of being taken via the oral route of administration.

For purposes of the present invention, "dry powder" shall be understood to mean powders which are relatively dry to the touch a rather than powders which are essentially without moisture content.

DETAILED DESCRIPTION OF THE INVENTION

A first aspect of the invention includes powder mixtures which are useful in preparing film coatings. The film coatings preferably have pearlescent qualities and are typically applied as suspensions to orally ingestible substrates such as compressed tablets and the like using pan coating or spraying techniques well known to those of ordinary skill. The inventive powder mixtures include a cellulosic polymer, a detackifier, gloss enhancer(s), and a pearlescent pigment.

In most embodiments, the amount of cellulosic polymer included in the powder mixtures of the present invention is from about 25 to about 70% by weight. In some preferred embodiments, it ranges from about 35 to about 60% and more preferably ranges from about 40 to about 55%. A non-limiting list of suitable cellulosic polymers which can be used include, for example food grade and/or pharmaceutically acceptable products known to those of ordinary skill, including hydroxypropylmethylcellulose (HPMC), sodium carboxymethylcellulose (NaCMC), hydroxypropylcellulose, hydroxyethylcellulose, etc. and combinations thereof. Preferably the cellulosic polymer is NaCMC. Preferably the grade of NaCMC is one which is pharmaceutically acceptable as per USP, EP, JP, etc. guidelines and creates a substantially colorless solution upon hydration. Preferably, the NaCMC has a medium or, more preferably, low viscosity.

The detackifier included in the powder mixtures of the invention can be selected from among lecithins, stearic acid, polysorbates, glyceryl monostearate, sodium lauryl sulfate, poloxamers, monoglycerides, diglycerides and mixtures thereof. Preferably, the detackifier is lecithin, polysorbate 80, stearic acid, or combinations thereof. More preferably the detackifier is a lecithin such as soya lecithin. The detackifier is used principally to reduce the incidence of tablet-to-tablet sticking that can occur during the film coating of pharmaceutical tablets and the like using aqueous suspensions/dispersions based on the inventive compositions. The amount of detackifier present will depend upon need, but can broadly range from about 4 to about 12% by weight. Preferably, the range is from about 6 to about 10% and more preferably from about 7.5 to about 10%.

In certain aspects of the invention, the powder mixtures include (by weight) from about 0.5 to about 40% pearlescent pigment, preferably from about 4 to about 32% and more preferably from about 7 to about 30%. It will be understood, however that the amount of pearlescent pigment employed in the powder mixtures of the invention is dependent on the opacity of the specific pigment being utilized and is an amount which is sufficient or effective to impart an improved pearlescent outer coating to the surface of the substrate to be coated.

One of the keys to the present invention is the ability to impart improved pearlescence to the surface of edible articles. In this regard, the choice of pearlescent pigment included in the powder mixtures must take into account that the pigment portion should be one meeting or is capable of meeting all government approved requirements for human consumption. In one preferred embodiment of the invention, the pearlescent pigments included are based on titanium dioxide platelets, also known as platy $TiO_2$, such as those available from Engelhard and/or those described in U.S. Pat. No. 5,611,851, and U.S. Pat. No. 6,627,212, the disclosures of which are incorporated herein by reference. Such products can be referred to as platelets of titanium dioxide. A non-limiting list of suitable pearlescent platy $TiO_2$ pigments include green, blue, violet, red, gold, orange, and pearl. In an alternative aspect of this embodiment, the pearlescent pigment is a micaceous pearlescent pigment such as those containing mica coated with titanium dioxide, iron oxide, etc., combinations thereof and the like. Some preferred pearlescent pigments are those available under the trade name Candurin® from Merck KGaA, as mentioned above.

See also PCT publication number WO 00/03609, the disclosure of which is incorporated herein by reference. A non-limiting list of suitable pearlescent pigment products include Candurin silver fine, silver sheen, silver luster and sparkle silvers, etc. various sugar products like banana sugar or others having a white color and gold, red or blue highlights. Still others include those having various colors, e.g. reds, bronzes, coppers having glitter or luster finishes. The only limitation on the pearlescent pigments included in the powders and other formulations described herein is that they must be capable of being substantially homogeneously combined with the other ingredients and that they must be capable of providing a high pearlescent finished coating on the coated article without substantially negatively effecting the organoleptic qualities of the finished product.

Preferred gloss enhancers include maltodextrin, dextrose and combinations thereof. The amount of maltodextrin is broadly from about 1 to about 35% by weight, preferably from about 5 to about 25% and more preferably from about 10 to about 20% by weight. Similarly, the amount of dextrose can range from about 1 to about 45% by weight. Preferably, it ranges from about 10 to about 35% and more preferably from about 15 to about 30% by weight.

Furthermore, the powder mixtures may also include supplemental or auxiliary ingredients typically found in film coatings. A non-limiting list of such adjuvants include colorants, plasticizers, glidants, surfactants, suspension aids, sweeteners, flavorants, etc. and mixtures thereof. The colorants are present in amounts ranging from to about 0.001 to about 30% by weight and can be selected from among food or pharmaceutically-acceptable ingredients such as FD&C lakes, titanium dioxide and dyes. Secondary film formers such as sodium alginate, propylene glycol alginate, and polyvinylpyrrolidone can also be included. The powders may further include a flow aid such as talc, fumed silica, bentonite, edible hydrogenated vegetable oils, hydrogenated vegetable oil and waxes, etc and/or a surfactant such as a polysorbate, polyethylene oxide, or stearic acid.

The powder mixtures are prepared using standard dry blending or mixing techniques known to those of ordinary skill. For example, the ingredients are individually weighed, added to a suitable apparatus and blended for a sufficient time until a substantially uniform mixture of the ingredients is obtained. The time required to achieve such substantial uniformity will, of course, depend upon the batch size and apparatus used. If any of the powder formulation ingredients are liquids, they are added only after all of the dry ingredients have been sufficiently blended, and the combination of wet and dry ingredients is blended for an additional amount of time to ensure homogeneity once all of the liquid is introduced.

As mentioned above, batch sizes will vary upon need. A non-limiting list of suitable blending devices include diffusion blenders such as a cross flow, V-blender, or hub blender, available from Patterson-Kelly, or Convection blenders, such as Ruberg or CVM blenders, available from Azo and Readco, respectively, may be used. Blending of the aforementioned formulation may also be achieved by processing ingredients into a granular form to produce a non-dusting granular coating composition by methods including, but not limited to, wet massing, fluid bed granulation, spray granulation and dry compaction, roller compaction or slugging. Other manners of blending will be apparent to those of ordinary skill.

In another embodiment of the invention, there are provided pearlescent film coating compositions which include the powder mixtures described above. Such compositions are preferably aqueous suspensions/dispersions which can include from about 2 to about 20% and preferably from about 6 to about 12% by weight solids content. Any optional ingredients which are not part of the powder can be added to the suspension, either during the formation of the suspension described below, or as a supplemental step after the initial product has been formed.

For purposes of illustration and not limitation, an aqueous suspension having about a 7.5% solids content can be formed by dispersing 30 grams of a blended powder mixture described hereinabove into 370.0 grams of ambient temperature water. The water is weighed into a suitable vessel, i.e. one with a diameter approximately equal to the depth of the final suspension. A low shear mixer, preferably one having a mixing blade with a diameter about one third the diameter of the mixing vessel, is lowered into the water and turned on to create a vortex from the edge of the vessel down to about just above the mixing blade to prevent entrapment of air. The 30 grams of dry film coating composition is added to the vortex at a rate where there is no excessive build up of dry powder. The speed and depth of the mixing blade is adjusted to avoid air being drawn into the suspension so as to avoid foaming. The suspension is stirred at low speed, preferably 350 rpm or less, for a time sufficient to insure that a homogenous mixture is formed. Using the above batch size as a guide, about 45 minutes would be required. The suspension is then ready for spraying onto pharmaceutical, food and candy substrates. Those of ordinary skill will also realize that there are many ways of preparing a substantially homogenous mixture of the solids in water and that the scope of the invention is in no way dependent on the apparatus used.

In still further embodiments of the invention, there are provided orally-ingestible substrates having a pearlescent film coating as well as methods of coating ingestible substrates using the suspensions described herein. As will be described in the Examples below, the methods include applying the pearlescent film coating compositions (suspensions) to a surface of an orally ingestible substrate. The film coating can be applied as part of a pan coating or spray coating process commonly used to coat such articles. The amount of coating applied will depend upon several factors, including the substrate to be coated, the amount and color of the pearlescent pigment included in the suspension, the apparatus employed to apply the coating, etc. In most aspects of the invention, however the substrates will be coated to a theoretical weight gain of from about 0.25 to about 5.0%. Preferably, the theoretical weight gain is from about 0.5 to about 4.0% and more preferably, the theoretical weight gain is from about 1.0 to about 3.0% by weight of said substrate.

As mentioned above, the coating solutions of the present invention may also include auxiliary ingredients in addition to the powder mixture and the water. For example, the artisan may disperse a colorant, into the pearlescent film coating compositions prior to applying the film coating to the substrate.

The pearlescent-coated orally-ingestible substrates described above can also be made to include a subcoat film coating between the orally-ingestible substrate and the pearlescent film coating. The subcoat selected is preferably based on an edible film coating composition that is compatible with and adheres to both the orally-ingestible substrate and the pearlescent coating. Thus, the artisan may choose from a wide variety of pharmaceutical or food-acceptable coatings for use as subcoats in the present invention. In some embodiments, the coating solution/suspension used as the subcoat will contain a cellulosic polymer and, optionally a maltodextrin. A non-limiting list of suitable coatings include those sold under the tradenames OPADRY® and OPAGLOS® 2 and other film-coating systems manufactured by Colorcon of West Point, Pa. The subcoat may also be free of pigment or include a sufficient amount of pigment which imparts added luster or otherwise enhances the pearlescent coating applied to the food article. For example, one way of increasing the visual appeal of the final product is by dispersing a colorant into the subcoat film coating before it is applied to the orally-ingestible substrate. The subcoat is also applied to the substrate to provide from about a 0.5 to about a 5.0% weight gain to the orally-ingestible substrate.

Regardless of the method employed or the specific materials included in the film coating compositions, the orally-ingestible substrates of the present invention preferably have a gloss value of at least about 140 gloss units. In addition, the orally-ingestible pearlescent film coated substrates of the present invention also have a quantitative pearlescence measurement (change in $DE^*94(2,1)$ from 15–25 degrees) of at least about 10. Preferably, however, the inventive orally-ingestible substrates have both a gloss value of at least about 140 gloss units and a quantitative pearlescence measurement (change in $DE^*94$ from 15–25 degrees) of at least about 10.

EXAMPLES

The following examples serve to provide further appreciation of the invention but are not meant in any way to restrict the effective scope of the invention. All ingredients are expressed as being by weight.

Example 1

A preferred formulation for a Gold pearlescent inventive dry coating composition is the following:

| Component | Percent | grams |
|---|---|---|
| NaCMC | 48.00 | 48.00 |
| Maltodextrin | 19.00 | 19.00 |
| Dextrose Monohydrate | 15.00 | 15.00 |
| Soya Lecithin | 8.00 | 8.00 |
| Gold Platy $TiO_2$ | 10.00 | 10.00 |
| | 100.00 | 100.00 |

NaCMC, Maltodextrin, Dextrose and Soya Lecithin meet USP/EP/JP pharmaceutical requirements.

Formulation Preparation:

The film coating suspension is prepared by weighing all ingredients into a suitable-sized food processor/blender and blending for 5 minutes until a homogenous mixture is produced. The ingredients of this formulation are all dry powders, but in examples that may follow, if any formulation ingredients are liquids, they are added to the dry mixture after the initial 5 minute blend time and the total mixture is blended an additional 5 minutes once all liquid is introduced.

Formulation Hydration:

Thirty grams of the blended mixture is dispersed into 370.0 grams of ambient temperature water to make an aqueous coating suspension having a 7.5% solids content. The water is weighed into a vessel with the diameter approximately equal to the depth of the final suspension. A low shear mixer is lowered into the water and turned on to create a vortex from the edge of the vessel down to just above the mixing blade to prevent entrapment of air. The 30 grams of dry film coating composition is added to the vortex at a rate where there is no excessive build up of dry powder. The speed and depth of the mixing blade is adjusted to avoid air being drawn into the suspension so as to avoid foaming. The suspension is stirred at low speed, preferably 350 rpm or less, for 45 minutes and is then ready for spraying onto substrates like pharmaceutical tablets or food and candy substrates.

Formulation Coating:

A 1.0 kilogram mixed substrate charge containing 990.0 grams of ⅜" standard convex placebos and 10.0 grams of 1⅛" diameter placebo slugs, (manufacturing process and purpose as defined in a later section), is spray coated with the invention of this disclosure in an O'Hara LabCoat I fully perforated side-vented coating pan equipped with a 12" insert and 1-Spraying Systems JAU gun (¼ JAU-SS, 60/100SS nozzle and 134 255-45-SS air cap). The average coating parameters are: inlet temperature (IT) 63° C., exhaust temperature (ET) 43° C., coating bed temperature (BT) 43° C., airflow 120–130 cfm, air pressure –0.1 in. of water, fluid delivery rate (FDR) 8 g/min, Atomizing air pressure (AP) 35 psi, pan speed (PS) 18 rpm. A theoretical coating weight gain of 3.0% is applied to the tablets and the coated tablets are smooth, non-tacky, glossy and highly pearlescent in appearance with a gold finish. The values for gloss, pearlescence, luster, and color purity for the coated tablets of Example 1 and coated tablet samples from Examples 2–7 appear in FIG. 1.

Examples 2–7

Coating suspensions of dry formulations 2–7 as appearing below are prepared and hydrated at 7.5% solids as described in Example 1.

Examples 2–7 were film coated in a LabCoat I equipped with a 12" insert using the same substrates and conditions as described in Example 1. Final coated tablet appearance for all examples of these formulations are very glossy and highly pearlescent.

Comparison to Prior Art

To provide evidence that the enhanced pearlescence and gloss of the inventive formulations of this disclosure are superior and preferred over the prior art, a series of evaluations, both objective and subjective, were conducted on coated tablets of the invention and coated tablets of six other formulation backbones with inclusion of the same amount of pearlescent pigment. The values from these evaluations were ranked and compared to determine the best overall glossy and pearlescent tablet appearance. These evaluations and their methods are described in detail below.

Objective Measurements:

Measuring Color/Pearlescence/Luster/Color Purity/Gloss/Total Elegance Measuring Color Color of the highly pealescent coated tablets was measured using an X-Rite model MA68II Multi-Angle Spectrophotometer and X-Rite ColorMaster Software. The instrument uses 45° illumination from a gas filled tungsten lamp at approximately 3000° K. Readings are taken at 15°, 25°, 45°, 75°, and 110° from specular using a fiber optic pick-up with Dynamic Rotational sampling and Blue-Enhanced silicon photodiodes. The viewing area is 12.7 mm (½") in diameter. Data is generated over the 400 nm–700 nm range at 10 nm increments. The software computes $L^*$, $a^*$, $b^*$, $c^*$, and h values from the reflectance curves at each of the measurement angles. However, the instrument's measurement aperture is 23 mm (0.91") in diameter, which is significantly larger than the average pharmaceutical solid dosage form, so the placebo slugs of the following description were manufactured, coated, and used for measurement. The flat-faced coated slugs from the description below were placed over the instrument aperture, and two measurements were taken. The two reflectance spectra at each angle were averaged prior to computing the color parameters.

Manufacture of Slugs Used for Formula Evaluation

A placebo blend was prepared with the following composition: 48.625% microcrystalline cellulose, 48.625% Pregelatinized Corn Starch, 2% Stearic Acid, 0.5% Colloidal silicon dioxide (Cab-O-Sil), and 0.25% Magnesium Stearate. Five grams of the placebo blend was placed into a flat faced 1⅛" diameter die and compressed using a Carver Hydraulic press (Model C) for 15 seconds at 20,000 lbs force. Finished slugs were 1⅛" diameter by ¼" thick and were white.

Additional Placebos Used 320 mg tablets, were manufactured on a Manesty B4 30-station tablet press using the same blend mixture as described above. Tablets compressed are standard convex,

|  | Example Number | | | | | |
| --- | --- | --- | --- | --- | --- | --- |
|  | 2 | 3 | 4 | 5 | 6 | 7 |
|  | Blue | Green | Wine Red | Silver | Dark Gold | Dark Blue |
| Component | *Component Amount (g) | | | | | |
| Water | 370.0 | 370.0 | 370.0 | 370.0 | 370.0 | 370.0 |
| Na CMC | 14.4 | 14.4 | 14.4 | 14.4 | 14.4 | 14.4 |
| Maltodextrin | 5.7 | 5.7 | 5.7 | 5.7 | 5.6 | 5.6 |
| Dextrose Monohydrate | 4.5 | 4.5 | 4.5 | 4.5 | 4.5 | 4.5 |
| Lecithin | 2.4 | 2.4 | 2.4 | 2.4 | 2.4 | 2.4 |
| Blue Platy $TiO_2$ | 3.0 | 0.0 | 0.0 | 0.0 | 0.0 | 3.0 |
| Gold Platy $TiO_2$ | 0.0 | 0.0 | 0.0 | 0.0 | 3.0 | 0.0 |
| Green Platy $TiO_2$ | 0.0 | 3.0 | 0.0 | 0.0 | 0.0 | 0.0 |
| Candurin Wine Red | 0.0 | 0.0 | 3.0 | 0.0 | 0.0 | 0.0 |
| Candurin Silver Lustre | 0.0 | 0.0 | 0.0 | 3.0 | 0.0 | 0.0 |
| Yellow 5 dye | 0.0 | 0.0 | 0.0 | 0.0 | 0.1 | 0.0 |
| Blue 1 dye | 0.0 | 0.0 | 0.0 | 0.0 | 0.0 | 0.1 |
| Total coating solution | 400.0 | 400.0 | 400.0 | 400.0 | 400.0 | 400.0 |
| Wt. % solids in coating solution | 7.5% | 7.5% | 7.5% | 7.5% | 7.5% | 7.5% |

*All component amounts expressed in terms of parts by weight unless otherwise noted.

0.163" thick, 0.395" diameter, white, with and without debossed logo. These tablets were made to provide sufficient load for the pan coating of the slugs, which were the objects measured.

Pearlescence Calculation

Pearlescence is defined as a color that displays various colors depending on the angles of illumination and viewing, as in mother of pearl. It is calculated as the DE*94(2,1) change in color from 15° to 25° viewing angles from specular. DE*94 color tolerancing and its advantages over CIELAB are well known in the industry. Briefly, DE*94 color difference values directly address humans' perception that color difference tolerancing is elliptical rather than spherical in CIELAB color space and that the size of the acceptance region varies depending on its position within the color space. For example, in the orange areas, the ellipsoids are narrower than in the green areas because humans are more able to detect variations in hue in the orange region. Ellipsoids in the high chroma region are larger than the ellipsoids in the low chroma region for the same reason.

The DE*94 equation has three parameters ($k_L$, $k_C$, & $k_H$) to be adjusted for optimizing the correlation between calculated color differences and human perception. Because the $k_H$ parameter is commonly set to 1, $k_L$ & $k_C$ are commonly substituted with an 1:c ratio as is done in the X-Rite software. When all the reference conditions for the DE*94 equation are met, and the surface has no texture, 1 and c are commonly set to one. One such reference condition is that the CIELAB DE* color difference is less than 5 units. Because the tablet samples discussed here have CIELAB DE* color differences greater than 5, however, the 1 value in the DE*94 equation was set to 2, and the c value was left at 1. Color differences are reported here as DE*94(2,1).

For nacreous pigments, the interference color and opacity are most developed at the specular or gloss angle and decreases significantly as the viewing angle increases. The change in color with angle nearest to the gloss angle (i.e. 15° and 25°) are most appropriate for quantifying pearlescence. Higher values indicate higher pearlescence.

Luster Calculation

Luster depends on the variation of lightness with angle. It has nothing to do with color or shape, but is related to transparency, surface conditions, crystal habit, and index of refraction. Because no formal definition exists for quantifying luster of nacreous pigments, the mathematical definition for perceived metallic luster is used. Luster, S, is calculated as follows:

$S = 3*(L1-L3)/L2$, where L1 is the CIELAB L* value measured at 15° from specular, and L2 and L3 are the corresponding L* values measured at the 45° and 110° aspecular angles, respectively. Higher values indicate higher luster.

Color Purity

Also called chroma, c*, pure colors are those present in the spectrum when passing light through a prism at one angle. Colors not existing in the spectrum are obtained by blending pure colors. Pure colors have high values of c*; impure colors have low values of c*. With respect to the formulas compared, evaluated and tested in this patent disclosure that suggest lower purity, the presence of insoluble components in those formulations may scatter the light causing the colors to mix. The higher the value, (100 is highest), the more visible the pure color of the sample.

Measuring Gloss

Gloss is measured using a Tricor Systems' Model 801A Gloss/Surface Analysis System. Gloss values, measured in 'gloss units' (g.u.), are obtained by light reflection from coated tablets, irrespective of sample shape, texture or color. The unit operates on the principle that at the Brewster angle (measuring angle required for the refractive index of the material(s) being measured), specular reflection is 100% polarized in the perpendicular direction while diffuse reflection is 50% polarized in the perpendicular direction and 50% polarized in the parallel direction. Sixty tablets were placed face-up on a felt surface in the unit such that the illumination source and analysis camera satisfied the 57° angle requirement. The perpendicular component was obtained by recording a digital image after placing a polarizing filter in front of the camera. A second digital image was obtained by rotating the polarizing filter 90° to remove the specular component. Then a pixel-by-pixel subtraction was performed to arrive at the amount of specular reflection at each point above a threshold value of zero gloss. Gloss values are calculated using the average of the brightest 50% of the pixels above the threshold value, and that value is recorded. The higher the value the greater the gloss.

Ranking

The measurements for each of the objective determinations of the seven film coated tablets, Gloss, Pearlescence, Luster, and Color Purity, are ranked from highest to lowest value in each category. This ranking is used to determine the 'Total Elegance' of the film coating. 'Total Elegance' Factor is a term derived for the averaged ranking of the quantitative measurements for the four film coating appearance indicators, gloss, pearlescence, luster, and color purity. The elegance factor value closest to 1.0 indicates coated tablets with the best overall appearance.

Subjective Measurements:

Visual Sensory Survey

Approximately 160–180 tablets were placed in open dishes for viewing in a light booth (MacBeth, SpectraLight) under Day and UV illumination. In this double blind study, tablets coated with the formulations to be evaluated, were arranged such that all samples of the same color were in rows for easy comparison. Thirteen study participants were asked to select the tablet sample for each color group exhibiting the highest combination of pearlescence, gloss, and luster. The percentage of respondents who chose a given sample is recorded.

Formulation Evaluation:

The calculated values for Examples 1–7 appear in the table below. In comparison with the six formulations of the prior art to follow, the overall elegance factor for the formulas of this disclosure have the highest rankings among all formulations tested. Gloss, Pearlescence, Luster, and Color Purity calculations for these formulas are outlined in Table 1:

TABLE 1

Tablet Appearance Evaluation of Preferred Formulations

| Example Number/ Pearlescent Color | Gloss (g.u.) | Pearlescence (Change in DE*94 [2,1] from 15°–25°) | Luster (Change in L* w/angle) | Color Purity (c* @ 15°) |
|---|---|---|---|---|
| Example 1/Gold | 175 | 13.46 | 1.89 | 46.84 |
| Example 2/Blue | 169 | 20.13 | 0.89 | 24.19 |
| Example 3/Green | 176 | 13.65 | 1.43 | 26.96 |
| Example 4/Wine Red | 166 | 16.14 | 7.87 | 41.08 |
| Example 5/Silver | 182 | 20.66 | 3.51 | 41.08 |
| Example 6/Dark Gold | 173 | 11.34 | 1.82 | 76.77 |
| Example 7/Dark Blue | 165 | 13.54 | 2.16 | 53.83 |

COMPARATIVE EXAMPLES

In order to compare the tablet appearance data in the above table for the formulas of this disclosure to other film coating systems well known in the art, the following comparative examples were prepared, film coated, and evaluated. Evaluations for pearlescence, gloss, luster and color purity appear in the tables following the comparative formulation tables.

Comparative Examples A1–A4

Opadry® Systems of U.S. Pat. No. 4,543,370

Examples A1–A4 are Opadry®-based systems, available form Colorcon, West Point, Pa. and were hydrated and film coated in an O'Hara LabCoat I equipped with a 12" insert using the same substrates and conditions as described in Example 1. Final coated tablet appearance for all examples of these formulations are glossy and pearlescent, but do not have the same amount of elegance as compared to the invention of this disclosure.

|  | Example Number | | | |
| --- | --- | --- | --- | --- |
|  | A1 | A2 | A3 | A4 |
|  | Blue | Gold | Wine Red | Silver |
| Component | *Component Amount (g) | | | |
| Water | 370.0 | 370.0 | 370.0 | 370.0 |
| HPMC, U.S.P., 6 cP | 24.2 | 24.2 | 24.2 | 24.2 |
| Polyethylene Glycol 400 | 1.4 | 1.4 | 1.4 | 1.4 |
| Polyethylene Glycol 8000 | 1.4 | 1.4 | 1.4 | 1.4 |
| Blue Platy TiO$_2$ | 3.0 | 0.0 | 0.0 | 0.0 |
| Gold Platy TiO$_2$ | 0.0 | 3.0 | 0.0 | 0.0 |
| Candurin Wine Red | 0.0 | 0.0 | 3.0 | 0.0 |
| Candurin Silver Lustre | 0.0 | 0.0 | 0.0 | 3.0 |
| Total coating solution | 400.0 | 400.0 | 400.0 | 400.0 |
| Wt. % solids in coating solution | 7.5% | 7.5% | 7.5% | 7.5% |

*All component amounts are expressed in terms of parts by weight unless otherwise noted.

Comparative Examples B1–B4

NaCMC/PEG Systems of U.S. Pat. No. 4,931,286

Examples B1–B4 are based on NaCMC/PEG and were hydrated and film coated in an O'Hara LabCoat I equipped with a 12" insert using the same substrates and conditions as described in Example 1. Final coated tablet appearance for all examples of these formulations are glossy and somewhat pearlescent, but do not have the same amount of elegance as compared to the inventive compositions.

|  | Example Number | | | |
| --- | --- | --- | --- | --- |
|  | B1 | B2 | B3 | B4 |
|  | Blue | Gold | Wine Red | Silver |
| Component | *Component Amount (g) | | | |
| Water | 370.0 | 370.0 | 370.0 | 370.0 |
| Na CMC | 22.4 | 22.4 | 22.4 | 22.4 |
| Polyethylene Glycol 400 | 4.6 | 4.6 | 4.6 | 4.6 |
| Subdued Blue Pigment | 3.0 | 0.0 | 0.0 | 0.0 |
| Subdued Gold Pigment | 0.0 | 3.0 | 0.0 | 0.0 |
| Candurin Wine Red | 0.0 | 0.0 | 3.0 | 0.0 |
| Candurin Silver Lustre | 0.0 | 0.0 | 0.0 | 3.0 |
| Total coating solution | 400.0 | 400.0 | 400.0 | 400.0 |
| Wt. % solids in coating solution | 7.5% | 7.5% | 7.5% | 7.5% |

*All component amounts are expressed in terms of parts by weight unless otherwise noted.

Comparative Examples C1–C4

Opadry® AMB Systems of U.S. Pat. No. 6,495,163

Examples C1–C4 are Opadry® AMB-based systems and were hydrated and film coated in an O'Hara LabCoat I equipped with a 12" insert using the same substrates and conditions as described in Example 1 with the following exceptions: solids 15%, exhaust and bed temperature 45° C., FDR 6 g/min, AP 40 psi. Final coated tablet appearance for all examples of these formulations are only slightly glossy and pearlescent as compared to the invention of this disclosure.

|  | Example Number | | | |
| --- | --- | --- | --- | --- |
|  | C1 | C2 | C3 | C4 |
|  | Blue | Gold | Wine Red | Silver |
| Component | *Component Amount (g) | | | |
| Water | 170.0 | 170.0 | 170.0 | 170.0 |
| Polyvinyl Alcohol | 17.6 | 17.6 | 17.6 | 17.6 |
| Talc | 8.0 | 8.0 | 8.0 | 8.0 |
| Soya Lecithin | 1.2 | 1.2 | 1.2 | 1.2 |
| Xanthan Gum | 0.1 | 0.1 | 0.1 | 0.1 |
| Blue Platy TiO$_2$ | 3.0 | 0.0 | 0.0 | 0.0 |
| Gold Platy TiO$_2$ | 0.0 | 3.0 | 0.0 | 0.0 |
| Candurin Wine Red | 0.0 | 0.0 | 3.0 | 0.0 |
| Candurin Silver Lustre | 0.0 | 0.0 | 0.0 | 3.0 |
| Total coating solution | 200.0 | 200.0 | 200.0 | 200.0 |
| Wt. % solids in coating solution | 15.0% | 15.0% | 15.0% | 15.0% |

*All component amounts are expressed in terms of parts by weight unless otherwise noted.

Comparative Examples D1–D4

Opadry® II Systems of U.S. Pat. No. 6,448,323

Examples D1–D4 are Opadry® II-based systems, also a product of Colorcon, and were hydrated and film coated in an O'Hara LabCoat I equipped with a 12" insert using the same substrates and conditions as described in Example 1 with the following exceptions: solids 15%, exhaust and bed temperature 45° C., FDR 6 g/min, AP 40 psi. Final coated tablet appearance for all examples of these formulations are of moderate gloss and pearlescence as compared to the invention of this disclosure.

|  | Example Number | | | |
| --- | --- | --- | --- | --- |
|  | D1 | D2 | D3 | D4 |
|  | Blue | Gold | Wine Red | Silver |
| Component | *Component Amount (g) | | | |
| Water | 170.0 | 170.0 | 170.0 | 170.0 |
| Polyvinyl Alcohol | 14.9 | 14.9 | 14.9 | 14.9 |
| Talc | 6.8 | 6.8 | 6.8 | 6.8 |
| Soya Lecithin | 1.2 | 1.2 | 1.2 | 1.2 |
| Peg 3000 | 4.2 | 4.2 | 4.2 | 4.2 |
| Blue Platy TiO$_2$ | 3.0 | 0.0 | 0.0 | 0.0 |
| Gold Platy TiO$_2$ | 0.0 | 3.0 | 0.0 | 0.0 |
| Candurin Wine Red | 0.0 | 0.0 | 3.0 | 0.0 |
| Candurin Silver Lustre | 0.0 | 0.0 | 0.0 | 3.0 |
| Total coating solution | 200.0 | 200.0 | 200.0 | 200.0 |
| Wt. % solids in coating solution | 15.0% | 15.0% | 15.0% | 15.0% |

*All component amounts are expressed in terms of parts by weight unless otherwise noted.

Comparative Examples E1–E4

Acryl-EZE® Systems of U.S. Pat. No. 6,420,473

Examples E1–E4 are Acryl-EZE®-based systems, available from Colorcon, and were hydrated and film coated in an O'Hara LabCoat I equipped with a 12" insert using the same substrates and conditions as described in Example 1 with the following exceptions: solids 20%, inlet temperature 370° C., exhaust temperature 33° C., bed temperature 30° C., AP 30 psi. Additionally, hydrated solution was passed through a 60 mesh sieve prior to coating. Final coated tablet appearance for all examples of these formulations are of minimal gloss and pearlescence as compared to the invention of this disclosure.

conditions as described in Example 1 with the following exceptions: solids 12%, FDR 7 g/min. Final coated tablet appearance for all examples of these formulations are only slightly glossy and pearlescent as compared to the invention of this disclosure.

|  | Example Number | | | |
| --- | --- | --- | --- | --- |
|  | E1 | E2 | E3 | E4 |
|  | Blue | Gold | Wine Red | Silver |
| Component | *Component Amount (g) | | | |
| Water | 120.0 | 120.0 | 120.0 | 120.0 |
| **Eudragit L-100/55 NF, EP | 12.0 | 12.0 | 12.0 | 12.0 |
| Talc | 11.2 | 11.2 | 11.2 | 11.2 |
| Triethyl Citrate | 2.9 | 2.9 | 2.9 | 2.9 |
| Colloidal Silicon Dioxide | 0.4 | 0.4 | 0.4 | 0.4 |
| Sodium Bicarbonate | 0.4 | 0.4 | 0.4 | 0.4 |
| Sodium Lauryl Sulfate | 0.002 | 0.002 | 0.002 | 0.002 |
| Blue Platy $TiO_2$ | 3.0 | 0.0 | 0.0 | 0.0 |
| Gold Platy $TiO_2$ | 0.0 | 3.0 | 0.0 | 0.0 |
| Candurin Wine Red | 0.0 | 0.0 | 3.0 | 0.0 |
| Candurin Silver Lustre | 0.0 | 0.0 | 0.0 | 3.0 |
| Total coating solution | 200.0 | 200.0 | 200.0 | 200.0 |
| Wt. % solids in coating solution | 20% | 20% | 20% | 20% |

*All component amounts are expressed in terms of parts by weight unless otherwise noted.
**Eudragit L-100/55 is methacrylic acid copolymer available from Röhm.

Comparative Examples F1–F4

HPMC/MCC Systems of U.S. Pat. No. 4,576,646

Examples F1–F4 are HPMC/MCC based systems and were hydrated and film coated in an O'Hara LabCoat I equipped with a 12" insert using the same substrates and

|  | Example Number | | | |
| --- | --- | --- | --- | --- |
|  | F1 | F2 | F3 | F4 |
|  | Blue | Gold | Wine Red | Silver |
| Component | *Component Amount (g) | | | |
| Water | 230.0 | 230.0 | 230.0 | 230.0 |
| HPMC, U.S.P., 6 cP | 13.5 | 13.5 | 13.5 | 13.5 |
| Microcrystalline Cellulose | 10.8 | 10.8 | 10.8 | 10.8 |
| Stearic Acid Powder | 2.7 | 2.7 | 2.7 | 2.7 |
| Subdued Blue Pigment | 3.0 | 0.0 | 0.0 | 0.0 |
| Subdued Gold Pigment | 0.0 | 3.0 | 0.0 | 0.0 |
| Candurin Wine Red | 0.0 | 0.0 | 3.0 | 0.0 |
| Candurin Silver Lustre | 0.0 | 0.0 | 0.0 | 3.0 |
| Total coating solution | 260.0 | 260.0 | 260.0 | 260.0 |
| Wt. % solids in coating solution | 12% | 12% | 12% | 12% |

*All component amounts are expressed in terms of parts by weight unless otherwise noted.

Comparative Data Tables

The following compares the collected data for the seven formulations. The first column in the tables contains values for the inventive formulations.

| | | Gold Formulations | | | | | | |
| --- | --- | --- | --- | --- | --- | --- | --- | --- |
| Film Coating System Example | | Ex1 | A2 | B2 | C2 | D2 | E2 | F2 |
| Gloss (gu) | Value | 175 | 151 | 171 | 115 | 124 | 112 | 99 |
|  | Rank | 1 | 3 | 2 | 5 | 4 | 6 | 7 |
| Pearlescence (change in DE*94 [2, 1] from 15°–25°) | Value | 13.46 | 12.48 | 12.23 | 3.86 | 6.27 | 5.41 | 4.53 |
|  | Rank | 1 | 2 | 3 | 7 | 4 | 5 | 6 |
| Luster (change in L* from 15°–25°) | Value | 1.89 | 1.87 | 1.67 | 0.87 | 1.1 | 1.05 | 0.93 |
|  | Rank | 1 | 2 | 3 | 7 | 4 | 5 | 6 |
| Color Purity (c* @ 15°) | Value | 46.84 | 40.25 | 39.07 | 22.23 | 29 | 27.14 | 26.73 |
|  | Rank | 1 | 2 | 3 | 7 | 4 | 5 | 6 |
| Overall Elegance Factor | | 1 | 2.25 | 2.75 | 6.6 | 4 | 5.25 | 6.25 |
| Visual survey results n = 13 (%) | | 69.2% | 7.7% | 23.1% | 0.0% | 0.0% | 0.0& | 0.0% |

| | | Blue Formulations | | | | | | |
| --- | --- | --- | --- | --- | --- | --- | --- | --- |
| Film Coating System Example | | Ex2 | A1 | B1 | C1 | D1 | E1 | F1 |
| Gloss (gu) | Value | 169 | 143 | 157 | 111 | 116 | 126 | 100 |
|  | Rank | 1 | 3 | 2 | 6 | 5 | 4 | 7 |
| Pearlescence (change in DE*94 [2, 1] from 15°–25°) | Value | 20.13 | 18.25 | 18.25 | 4.25 | 9.06 | 8.49 | 5.79 |
|  | Rank | 1 | 2 | 2 | 6 | 3 | 4 | 5 |
| Luster (change in L* from 15°–25°) | Value | 0.89 | 0.86 | 0.74 | 0.58 | 0.71 | 0.67 | 0.52 |
|  | Rank | 1 | 2 | 3 | 6 | 4 | 5 | 7 |

-continued

| | | Blue Formulations | | | | | | |
|---|---|---|---|---|---|---|---|---|
| Film Coating System Example | | Ex2 | A1 | B1 | C1 | D1 | E1 | F1 |
| Color Purity | Value | 24.19 | 29.02 | 25.47 | 1.87 | 9.26 | 7.2 | 4.23 |
| ($c*$ @ 15°) | Rank | 3 | 1 | 2 | 7 | 4 | 5 | 6 |
| Overall Elegance Factor | | 1.5 | 2 | 2.25 | 6.25 | 4 | 4.5 | 6.25 |
| Visual survey results n = 13 (%) | | 76.9% | 7.7% | 15.4% | 0.0% | 0.0% | 0.0% | 0.0% |

| | | Wine Red Formulations | | | | | | |
|---|---|---|---|---|---|---|---|---|
| Film Coating System Example | | Ex4 | A3 | B3 | C3 | D3 | E3 | F3 |
| Gloss (gu) | Value | 166 | 149 | 160 | 116 | 121 | 118 | 92 |
| | Rank | 1 | 3 | 2 | 6 | 4 | 5 | 7 |
| Pearlescence (change | Value | 16.14 | 13.79 | 14.3 | 5.71 | 9.48 | 8.55 | 5.48 |
| in $DE*94$ [2,1] from | Rank | 1 | 3 | 2 | 6 | 4 | 5 | 7 |
| 15°–25°) | | | | | | | | |
| Luster (change in $L*$ | Value | 7.87 | 6.9 | 6.67 | 2.45 | 4.39 | 3.99 | 2.24 |
| from 15°–25°) | Rank | 1 | 2 | 3 | 6 | 4 | 5 | 7 |
| Color Purity | Value | 41.08 | 34.79 | 33.92 | 20.3 | 25.95 | 28.27 | 24.88 |
| ($c*$ @ 15°) | Rank | 1 | 2 | 3 | 7 | 5 | 4 | 6 |
| Overall Elegance Factor | | 1 | 2.5 | 2.5 | 6.25 | 4.25 | 4.75 | 6.75 |
| Visual survey results n = 13 (%) | | 61.5% | 23.1% | 15.4% | 0.0% | 0.0% | 0.0% | 0.0% |

| | | Silver Formulations | | | | | | |
|---|---|---|---|---|---|---|---|---|
| Film Coating System Example | | Ex5 | A4 | B4 | C4 | D4 | E4 | F4 |
| Gloss (gu) | Value | 182 | 164 | 182 | 108 | 132 | 135 | 105 |
| | Rank | 1 | 2 | 1 | 5 | 4 | 3 | 6 |
| Pearlescence (change | Value | 20.66 | 18.85 | 15.55 | 4.26 | 9.66 | 10.16 | 6.13 |
| in $DE*94$ [2,1] from | Rank | 1 | 2 | 3 | 7 | 5 | 4 | 6 |
| 15°–25°) | | | | | | | | |
| Luster (change in $L*$ | Value | 3.51 | 3.1 | 2.29 | 0.91 | 1.7 | 1.95 | 1.09 |
| from 15°–25°) | Rank | 1 | 2 | 3 | 7 | 5 | 4 | 6 |
| Color Purity | Value | 2.56 | 1.2 | 1.32 | 1.53 | 0.54 | 1.01 | 0.62 |
| ($c*$ @ 15°) | Rank | 1 | 4 | 2 | 3 | 7 | 5 | 6 |
| Overall Elegance Factor | | 1 | 2.5 | 2.25 | 5.5 | 5.25 | 4 | 6 |
| Visual survey results n = 13 (%) | | 84.6% | 7.7% | 7.7% | 0.0% | 0.0% | 0.0% | 0.0% |

As can be seen in the comparative data tables, Examples 1, 2, 4, and 5, which correspond to formulations of the invention of this disclosure, have the highest overall elegance factor in four separate pigmented studies, and have the highest percentage of preferred visual response.

Example 8

A preferred formulation for a Blue pearlescent inventive dry coating composition is the following:

| Component | Percent | grams |
|---|---|---|
| NaCMC | 49.30 | 49.30 |
| Maltodextrin | 19.60 | 19.60 |
| Dextrose Monohydrate | 16.60 | 16.60 |
| Soya Lecithin | 7.50 | 7.50 |
| Blue Platy $TiO_2$ | 7.00 | 7.00 |
| | 100.00 | 100.00 |

This formulation is prepared and hydrated at 7.5% solids as in Example 1. A 1.0 kilogram charge of Acetaminophen caplets is previously film coated with a theoretical 3% weight gain of red pigmented film coating made from an Opaglos® 2 coating composition, [formula 97W15316], manufactured by Colorcon, West Point, Pa., and made in accordance with U.S. Pat. No. 6,274,162. These subcoated caplets, which register 195 gloss units after application of the Opaglos® 2, are further spray coated with the invention of this disclosure as described in Example 1. An additional theoretical coating weight gain ($wg_T$) of 3.0% is applied to the tablets and the coated tablets are smooth, non-tacky, highly glossy (236 gloss units) and highly pearlescent in appearance with a purple finish. The combination of red subcoat and blue pearlescent topcoat created a highly pearlescent purple tablet.

Example 9

1.250 kilograms of the formulation of Example 8 is prepared and hydrated into 15.42 kilograms of water to create a solution of 7.5% solids content as in Example 1, and spray coated onto a 125 kg charge of oval placebos. The oval tablets were previously sub-coated with a 2.75% actual weight gain ($wg_A$) of a purple pigmented film coating made from an Opadry® coating composition, manufactured by Colorcon and made in accordance with U.S. Pat. No. 4,543, 370. The pearlescent film coating takes place in a Freund Hi-Coater HCF-130, semi-perforated coating pan, equipped with 4 Freund Guns (012/025 Nozzle/cap), and a PU-GPA flow control pump. Gun to gun distance is 5.5", airflow is 1000–1200 cfm, IT is 75° C., ET is 45° C., BT is 43° C. FDR~150–170 g/min, PS is 6 rpm. A 0.78% $wg_A$ of the blue pearlescent coating is applied, and the final coated tablets are uniformly and highly pearlescent and glossy, (187 gloss units), with a bluish purple appearance.

Example 10

A preferred formulation for a Red pearlescent inventive dry coating composition is the following:

| Component | Percent | grams |
|---|---|---|
| NaCMC | 46.40 | 460.40 |
| Maltodextrin | 14.90 | 140.90 |
| Dextrose Monohydrate | 15.20 | 150.20 |
| Red Platy TiO$_2$ | 12.50 | 70.00 |
| Soya Lecithin | 7.50 | 70.50 |
| Vanillin | 3.50 | 30.50 |
|  | 100.00 | 1000.00 |

510.0 grams of the above inventive formulation is prepared and hydrated into 6290.0 grams of water to create a solution of 7.5% solids content as in Example 1, and spray coated onto a 17.0 kg charge of ⅜" standard convex placebos previously subcoated with 3.0% $wg_T$ of a pink pigmented film coating made from an Opadry® II coating composition, manufactured by Colorcon and made in accordance with U.S. Pat. No. 5,630,871. in an O'Hara LabCoat II fully perforated coating pan with 24" insert. The pan is equipped with 2-Spraying Systems® ¼ VAU spray guns (1282125-60-SS air cap w/3.25 mm diameter, 60100-SS fluid cap w/1.52 mm diameter) and 4 mixing baffles. Coating conditions are IT 80° C., ET 45° C., BT 43° C., FDR 48 g/min, AP 1.4 bar, pattern air pressure 2.1 bar, PS 12 rpm. Tablets are coated to a 3.0% $wg_T$, with sample tablets removed at the following weight % intervals: 0.25%, 0.5%, 0.75%, 1.0%, 1.5%, 2.0%, and 2.5%. Because of the different amounts of dry ingredients applied in the samples obtained, all tablet samples exhibit varying degrees of reddish-pink pearlescence and gloss as well as different intensity aromas of vanilla. This example illustrates the variety of tablet presentations that are possible depending on percent weight of the inventive composition applied over a subcoated tablet.

Example 11

Further to Example 10, a preferred formulation for a Green pearlescent inventive dry coating composition is the following:

| Component | Percent | grams |
|---|---|---|
| NaCMC | 48.00 | 48.00 |
| Maltodextrin | 19.00 | 19.00 |
| Dextrose Monohydrate | 15.00 | 15.00 |
| Soya Lecithin | 8.00 | 8.00 |
| Green Platy TiO$_2$ | 10.00 | 10.00 |
|  | 100.00 | 100.00 |

90.0 grams of the above inventive formulation is prepared and hydrated into 1110 grams of water to create a 7.5% solids solution as described in Example 1. 3.0 kilograms of a mixed load of various shaped placebo substrates, (triangles, ovals, hexagons, diamonds, teardrops, and rounds of between 200 mg and 335 mg total tablet weight), previously sub-coated with a 3.25% actual weight gain ($wg_A$) of a blue pigmented film coating made from an Opadry® NS coating composition, [formula 79G10865 manufactured by Colorcon and made in accordance with U.S. Pat. No. 6,348,090 are charged into a O'Hara LabCoat II fully perforated coating pan equipped with 15" insert and 1 SS ¼ VAU gun (1282125-60-SS air cap w/3.25 mm diameter, 60100-SS fluid cap w/1.52 mm diameter) and 4 mixing baffles. Coating conditions are same as those in Example 10 with these exceptions FDR 14 g/min, PS 16 rpm. Tablets are coated with a 3.0% $wg_T$, with sample tablets removed at the following weight % intervals: 0.5%, and 1.0%. All tablet samples exhibit varying degrees of teal to blue-green pearlescence and gloss.

Example 12

A preferred formulation for a Violet pearlescent inventive dry coating composition is the following:

| Component | Percent | grams |
|---|---|---|
| NaCMC | 49.30 | 49.30 |
| Maltodextrin | 19.60 | 19.60 |
| Dextrose Monohydrate | 16.60 | 16.60 |
| Soya Lecithin | 7.50 | 7.50 |
| Violet Platy TiO$_2$ | 7.00 | 7.00 |
|  | 100.00 | 100.00 |

This formulation is prepared and hydrated at 7.5% solids as in Example 1. A 1.0 kilogram charge of Ibuprofen tablets is previously film coated with a theoretical 3% weight gain of a rose colored film coating made from an Opadry® II coating composition, [formula 33G24219 manufactured by Colorcon, West Point Pa., and made in accordance with U.S. Pat. No. 5,743,947. These subcoated tablets are further spray coated with a total dry coating application of 10.0 grams of the invention of this disclosure as described in Example 1 to 1.0% $wg_T$ and the coated tablets are smooth, non-tacky, highly glossy (200 gloss units) and highly pearlescent in appearance with a violet-red finish.

Example 13

A preferred formulation for a Gold pearlescent inventive dry coating composition is the following:

| Component | Percent | grams |
|---|---|---|
| NaCMC | 49.30 | 49.30 |
| Maltodextrin | 26.10 | 26.10 |
| Dextrose Monohydrate | 16.60 | 16.60 |
| Soya Lecithin | 7.50 | 7.50 |
| Gold Platy TiO$_2$ | 0.50 | 0.50 |
|  | 100.00 | 100.00 |

Six grams (6.0 g) of the above formulation is dispersed in 74.0 grams of deionized water and the resultant 7.5% solids dispersion is spray coated in an Aeromatic fluidized bed coater with 1.1 mm fluid nozzle. Three-hundred (300) grams of ⅜" placebo tablets previously subcoated with a lime green Opadry® II subcoat, are used as the substrate and the pearlescent coating of this invention is coated to 2.0% $wg_T$. The coating parameters are inlet 60° C., outlet 40° C., atomizing air 1.5 bar, fluid delivery rate 6 g/min. The resultant tablets are smooth and glossy, (191 gloss units), with a subtle gold shimmer.

Example 14

A preferred formulation for a Gold pearlescent inventive dry coating composition is the following:

| Component | Percent | grams |
|---|---|---|
| NaCMC | 45.00 | 45.00 |
| Maltodextrin | 21.00 | 21.00 |
| Dextrose Monohydrate | 14.00 | 14.00 |
| Soya Lecithin | 10.00 | 10.00 |
| Titanium Dioxide | 6.00 | 9.50 |
| D&C Yellow 10 dye | 0.13 | 0.13 |
| Gold Platy TiO$_2$ | 4.00 | 0.50 |
| | 100.0 | 100.00 |

Nine (9) grams of the above formulation is dispersed in 111.0 grams of deionized water and the resultant 7.5% solids dispersion is spray coated in an Aeromatic fluidized bed coater with 1.1 mm fluid nozzle. Three hundred (300) grams of ⅜" uncoated placebo tablets are used as the substrate and the pearlescent coating of this invention is coated to 3.0% $wg_T$. The coating parameters are inlet 60° C., outlet 40° C., atomizing air 1.5 bar, fluid delivery rate 6 g/min. The resultant tablets are pale yellow, smooth and glossy, (179 gloss units), with a subtle gold shimmer.

Example 15

A preferred formulation for a Silver pearlescent inventive dry coating composition is the following:

| Component | Percent | grams |
|---|---|---|
| NaCMC | 49.30 | 49.30 |
| Maltodextrin | 19.60 | 19.60 |
| Dextrose Monohydrate | 16.60 | 16.60 |
| Soya Lecithin | 7.50 | 7.50 |
| Blue Platy TiO$_2$ | 3.71 | 3.71 |
| Green Platy TiO$_2$ | 1.89 | 1.89 |
| Gold Platy TiO$_2$ | 1.40 | 1.40 |
| | 100.00 | 100.00 |

This formulation is prepared and hydrated at 7.5% solids as in Example 1. A 1.0 kilogram charge of 9 mm deep convex placebo tablets, previously film coated with a theoretical 3% weight gain of a gray colored film coating made from an Opadry® II coating composition, are charged into an O'Hara LabCoat I coating pan equipped with 12" insert, 4 mixing baffles, and 1 SS ¼ VAU gun (134255-45-SS air cap and 60100-SS fluid cap). The tablets are further spray coated with a total dry coating application of 15.0 grams of the invention of this disclosure as described in Example 1 to 1.5% $wg_T$. Coating conditions are Inlet 55° C., Bed Temperature 44° C., FDR 9 g/min, Atomizing Air 30 psi, Pan Speed 18 rpm and the coated tablets are smooth, non-tacky, highly glossy (194 gloss units) and highly pearlescent in appearance with a silver finish.

Examples 16–23

The following table illustrates a small sampling of the variety of color combinations that can be created by using various color subcoats, and/or additions of other pigments and the pearlescent coatings of this disclosure. Additionally, as explained in Examples 10 and 11 but not illustrated in the table, the amount of pearlescent coating applied (% weight gain) will further widen the palette of potential color combinations. All formulations of these examples were prepared, hydrated, and coated as explained in previous examples depending on coating pan size. All coatings were applied to ⅜" standard convex placebo cores and all coated tablets were highly pearlescent and glossy.

Formula Ranges of Invention

| Component of Invention of this Disclosure | 16 Wine Red | 17 Bronze | 18 Silver | 19 Lavender | 20 Purple | 21 Wine Red | 22 Gold | 23 Lime Green |
|---|---|---|---|---|---|---|---|---|
| | \*Component Amount (%) | | | | | | | |
| Na CMC | 40.0 | 52.8 | 45.0 | 45.0 | 48.0 | 46.4 | 30.0 | 40.0 |
| Maltodextrin | 10.0 | 17.2 | 0.0 | 35.0 | 19.0 | 20.2 | 15.0 | 10.0 |
| Dextrose Monohydrate | 30.0 | 15.0 | 35.0 | 0.0 | 15.0 | 16.9 | 11.0 | 30.0 |
| Soya Lecithin | 10.0 | 8.0 | 10.0 | 10.0 | 8.0 | 4.0 | 4.0 | 10.0 |
| Red Platy TiO$_2$ | 0.0 | 0.0 | 0.0 | 0.0 | 4.0 | 12.5 | 0.0 | 0.0 |
| Gold Platy TiO$_2$ | 0.0 | 7.0 | 0.0 | 0.0 | 0.0 | 0.0 | 0.0 | 0.0 |
| Blue Platy TiO$_2$ | 0.0 | 0.0 | 0.0 | 0.0 | 6.0 | 0.0 | 0.0 | 0.0 |
| Candurin Butter Gold | 0.0 | 0.0 | 0.0 | 0.0 | 0.0 | 0.0 | 40.0 | 0.0 |

-continued

Formula Ranges of Invention

| Component of Invention of this Disclosure | Example Number | | | | | | | |
|---|---|---|---|---|---|---|---|---|
| | 16 Wine Red | 17 Bronze | 18 Silver | 19 Lavender | 20 Purple | 21 Wine Red | 22 Gold | 23 Lime Green |
| | *Component Amount (%) | | | | | | | |
| Candurin Wine Red | 10.0 | 0.0 | 0.0 | 0.0 | 0.0 | 0.0 | 0.0 | 0.0 |
| Candurin Silver Lustre | 0.0 | 0.0 | 10.0 | 0.0 | 0.0 | 0.0 | 0.0 | 0.0 |
| Candurin Kiwi Sugar | 0.0 | 0.0 | 0.0 | 0.0 | 0.0 | 0.0 | 0.0 | 10.0 |
| Candurin Blueberry Sugar | 0.0 | 0.0 | 0.0 | 10.0 | 0.0 | 0.0 | 0.0 | 0.0 |
| Red 40 dye | 0.0 | 0.0 | 0.0 | 0.0 | 0.0 | 0.2 | 0.0 | 0.0 |
| Formulation Totals | 100.0 | 100.0 | 100.0 | 100.0 | 100.0 | 100.0 | 100.0 | 100.0 |
| Wt. % solids in coating solution | 10.0% | 5.0% | 10.0% | 7.5% | 7.5% | 7.5% | 10.0% | 10.0% |
| % wg applied (theoretical) | 3.0% | 2.0% | 3.0% | 3.0% | 2.0% | 3.0% | 3.0% | 0.8% |
| Coating pan used | 15" | 12" | 15" | 12" | 12" | 15" | 12" | 12" |
| 3% wg subcoat used? (Y/N-Color) | N | Y-Brown | N | Y-Pink | Y-Black | N | N | Y-Yellow |
| Gloss units | 156 | 170 | 146 | 173 | 186 | 166 | 126 | 160 |

*All component amounts expressed in formula % unless otherwise noted.

Example 24

An alternate method to create the purple tablets from Example 20, (in table above), is by the following:

1.0 kilogram of ⅜" placebo tablets, previously coated to 3.0% wg with a black Opadry® II formulation, is charged into an O'Hara LabCoat I coating pan equipped with 12" insert, 4 mixing baffles, and 1 SS ¼ VAU gun (134255-45-SS air cap and 60100-SS fluid cap). The tablets are then spray coated as in Example 15 with a total dry coating application of 5.0 grams of a 7.5% solids dispersion of the pearlescent red formulation of Example 10. Immediately following, the now pearlescent red tablets are further coated to 0.75% $wg_T$ with a total dry coating application of 7.5 grams of a 7.5% solids dispersion of the pearlescent blue formulation of Example 8, to yield highly glossy (179 GU) pearlescent purple tablets.

Example 25

Oxygen Permeability Testing

Various film coating systems were subjected to Oxygen Transmission Testing for evaluation of their ability to prevent oxygen transfer to the core. The transmission rates were obtained using an OX-TRAN 2/20 (Mocon Inc. Minneapolis, Minn.) system utilizing a coulometric sensor to detect oxygen transmission through the free films. In this system, free films are clamped into a diffusion cell, which is then purged of residual oxygen using an oxygen-free carrier gas. Pure oxygen is then introduced into the outside chamber of the diffusion cell. Molecules of oxygen diffusing through the film to the inside chamber of the diffusion cell are conveyed to the coulometric sensor for detection. Each film was tested in duplicate and the data is reported as an average of the two tests along with the standard deviation. These films were tested under ambient temperature and 60% relative humidity. Film thicknesses ranged from 100–200 μm. The results are shown in the table below.

The data shows that the pearlescent systems of this disclosure possess excellent oxygen barrier properties and provide not only pleasing aesthetic appearance, but also functional protection for oxygen-labile cores.

Oxygen Transmission Rate Testing
Typical Tablet Film Coating Systems cc/(100 in$^2$ * day)

| Film Coating Formulation | Average Rate (n = 2) | Std. Deviation |
|---|---|---|
| Pigmented HPMC-based System | 27.100 | 0.424 |
| Clear HPMC-based System | 16.450 | 1.768 |
| Clear HEC-based System | 2.900 | 0.212 |
| Pigmented PVA/PEG-based System | 2.140 | 0.778 |
| Pigmented Methacrylic Acid-based System | 1.600 | 0.156 |
| White Methacrylic Acid-based System | 1.445 | 0.318 |
| White PVA-based System | 0.216 | 0.028 |
| White PVAP-based System | 0.199 | 0.037 |
| Clear NaCMC-based System | 0.159 | 0.026 |
| Pigmented NaCMC-based System | 0.019 | 0.030 |
| Example #8 of this disclosure | 0.016 | 0.001 |
| Example #9 of this disclosure | 0.013 | 0.001 |

What is claimed is:

1. A dry powder mixture for use in preparing film coating compositions, comprising a cellulosic polymer, a detackifier, a gloss enhancer comprising dextrose and a pearlescent pigment.

2. The powder mixture of claim 1, wherein said gloss enhancer further comprises maltodextrin.

3. The powder mixture of claim 2, wherein said maltodextrin is present in an amount of from about 1 to about 35% by weight.

4. The powder mixture of claim 3, wherein said maltodextrin is present in an amount of from about 5 to about 25% by weight.

5. The powder mixture of claim 4, wherein said maltodextrin is present in an amount of from about 10 to about 20% by weight.

6. The powder mixture of claim 2, wherein said dextrose is present in an amount of from about 1 to about 45% by weight.

7. The powder mixture of claim 6, wherein said dextrose is present in an amount of from about 10 to about 35% by weight.

8. The powder mixture of claim 7, wherein said dextrose is present in an amount of from about 15 to about 30% by weight.

9. The powder mixture of claim 1, wherein said cellulosic polymer is present in an amount of from about 25 to about 70% by weight.

10. The powder mixture of claim 9, wherein said cellulosic polymer is present in an amount of from about 35 to about 60% by weight.

11. The powder mixture of claim 10, wherein said cellulosic polymer is present in an amount of from about 40 to about 55% by weight.

12. The powder mixture of claim 1, wherein said cellulosic polymer is selected from the group consisting of hydroxypropylmethylcellulose and sodium carboxymethylcellulose.

13. The powder mixture of claim 1, wherein said cellulosic polymer is sodium carboxymethylcellulose.

14. The powder mixture of claim 1, wherein said detackifier is selected from the group consisting of lecithin, stearic acid, polysorbate 80 and combinations thereof.

15. The powder mixture of claim 1, wherein said detackifier is present in an amount of from about 4 to about 12% by weight.

16. The powder mixture of claim 15, wherein said detackifier is present in an amount of from about 6 to about 10% by weight.

17. The powder mixture of claim 16, wherein said detackifier is present in an amount of from about 7.5 to about 10% by weight.

18. The powder mixture of claim 1, wherein said pearlescent pigment is present in an amount of from about 0.5 to about 40% by weight.

19. The powder mixture of claim 18, wherein said pearlescent pigment is present in an amount of from about 4 to about 32% by weight.

20. The powder mixture of claim 19, wherein said pearlescent pigment is present in an amount of from about 7 to about 30% by weight.

21. The powder mixture of claim 1, wherein said pearlescent pigment is a micaceous pearlescent pigment.

22. The powder mixture of claim 21, wherein said pearlescent pigment is a mica coated with a member of the group consisting of titanium dioxide, iron oxide and combinations thereof.

23. The powder mixture of claim 1, wherein said pearlescent pigment comprises titanium dioxide platelets.

24. The powder mixture of claim 1, further comprising a member of the group consisting of colorants, plasticizers, glidants, surfactants, suspension aids, sweeteners, flavorants, and mixtures thereof.

25. The powder mixture of claim 24, wherein said colorants are present in an amount of from about 0.01 to about 30% by weight.

26. The powder mixture of claim 24, wherein said colorants are selected from the group consisting of FD&C lakes, D&C lakes, titanium dioxide, iron oxides and dyes.

27. A pearlescent film coating composition for film coating pharmaceutical substrates, comprising an aqueous suspension of the powder mixture of claim 1.

28. The pearlescent film coating composition of claim 27, wherein said suspension has from about 2 to about 20% solids.

29. The pearlescent film coating composition of claim 28, wherein said suspension has from about 6 to about 12% solids.

30. An orally-ingestible substrate having a pearlescent film coating, comprising an orally-ingestible substrate having the pearlescent film coating composition of claim 27 applied to a surface thereof.

31. The orally-ingestible substrate of claim 30, wherein said pearlescent film coating is applied to said pharmaceutical substrate to provide from about a 0.25 to about a 5.0% theoretical weight gain to said orally-ingestible substrate.

32. The orally-ingestible substrate of claim 31, wherein said theoretical weight gain is from about 0.5 to about 4.0% by weight of said substrate.

33. The orally-ingestible substrate of claim 32, wherein said theoretical weight gain is from about 1.0 to about 3.0% by weight of said substrate.

34. The orally-ingestible substrate of claim 30, further comprising a subcoat film coating between said orally-ingestible substrate and said pearlescent film coating.

35. The orally-ingestible substrate of claim 34, wherein said subcoat comprises an edible film coating composition that is compatible with and adheres to both the orally-ingestible substrate and the pearlescent coating.

36. The orally-ingestible substrate of claim 35, wherein said subcoat is applied to said pharmaceutical substrate to provide from about a 0.5 to about a 5.0% weight gain to said orally-ingestible substrate.

37. The orally-ingestible substrate of claim 35, wherein said subcoat comprises an edible film coating composition containing a cellulosic polymer.

38. The orally-ingestible substrate of claim 37, wherein said subcoat further comprises maltodextrin.

39. The orally-ingestible substrate of claim 30, wherein said pearlescent film coating has a gloss value of at least about 140 gloss units.

40. The orally-ingestible substrate of claim 30, wherein said pearlescent film coating has a quantitative pearlescence measurement (change in DE*94 (2,1) from 15–25 degrees) of at least about 10.

41. The orally-ingestible substrate of claim 30, wherein said pearlescent film coating has a gloss value of at least about 140 gloss units and a quantitative pearlescence measurement (change in DE*94 (2,1) from 15–25 degrees) of at least about 10.

42. A method of coating orally-ingestible substrates with a pearlescent film, comprising applying the pearlescent film coating composition of claim 30 to an orally-ingestible substrate.

43. The method of claim 42, further comprising dispersing a colorant into the pearlescent film coating suspension prior to applying said pearlescent film coating suspension to said orally ingestible substrate.

44. A coated substrate produced by the method of claim 42.

45. A method of coating orally-ingestible substrates with a pearlescent film, comprising applying a film coating subcoat to an orally-ingestible substrates to a theoretical weight gain of 0.5 to 5.0%; and thereafter applying the pearlescent film coating composition of claim 27 to the resultant subcoated orally-ingestible substrate.

46. The method of claim 45, further comprising dispersing a colorant into the pearlescent coating suspension before it is applied to the subcoated orally-ingestible substrate.

47. A coated substrate produced by the method of claim 46.

48. The powder mixture of claim 1, wherein said detackifier is selected from the group consisting of polysorbates, glyceryl monostearate, sodium lauryl sulfate, poloxamers, monoglycerides, diglycerides and mixtures thereof.

* * * * *

UNITED STATES PATENT AND TRADEMARK OFFICE
CERTIFICATE OF CORRECTION

PATENT NO.    : 6,902,609 B2
DATED         : June 7, 2005
INVENTOR(S)   : Rita M. Steffenino et al.

It is certified that error appears in the above-identified patent and that said Letters Patent is hereby corrected as shown below:

Title page,
Item [75], Inventors, delete "West Mailing", and insert -- West Malling --.
Item [56], References Cited, OTHER PUBLICATIONS, "Candurin® Unique Pigments" reference, delete "Merck KgaA", insert -- Merck KGaA --.

Column 2,
Line 58, between "touch" and "rather", delete "a".

Column 4,
Line 29, between "from" and "about", delete "to".

Column 8,
Line 10, the section heading "Measuring Color" should appear on a separate line.

Column 11,
Line 9, delete "form", insert -- from --.

Signed and Sealed this

Sixth Day of September, 2005

JON W. DUDAS
*Director of the United States Patent and Trademark Office*